United States Patent
Ngo et al.

(10) Patent No.: US 10,092,604 B1
(45) Date of Patent: Oct. 9, 2018

(54) METHODS FOR TREATMENT OF SKIN INFECTIOUS DISEASES USING MICROORGANISMS

(71) Applicant: BIOCEUTICALS PTE. LTD., Singapore (SG)

(72) Inventors: Dung Q Ngo, Ho Chi Minh (VN); Hoang H Dao, Ho Chi Minh (VN); Shoji Hanaoka, Hokkaido (JP); Yutaka Hasegawa, Hokkaido (JP); Tien T. Le, Ho Chi Minh (VN)

( * ) Notice: Subject to any disclaimer, the term of this patent is extended or adjusted under 35 U.S.C. 154(b) by 0 days.

(21) Appl. No.: 15/851,391

(22) Filed: Dec. 21, 2017

(51) Int. Cl.
| | | |
|---|---|---|
| *A61K 39/002* | (2006.01) | |
| *A61K 35/742* | (2015.01) | |
| *A61P 31/10* | (2006.01) | |
| *A61K 9/00* | (2006.01) | |
| *A61P 31/12* | (2006.01) | |
| *A61P 31/04* | (2006.01) | |
| *A61K 9/06* | (2006.01) | |
| *A61K 35/00* | (2006.01) | |

(52) U.S. Cl.
CPC .......... *A61K 35/742* (2013.01); *A61K 9/0014* (2013.01); *A61K 9/0019* (2013.01); *A61K 9/06* (2013.01); *A61P 31/04* (2018.01); *A61P 31/10* (2018.01); *A61P 31/12* (2018.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 9,540,407 | B2 * | 1/2017 | Maj | A61K 31/522 |
| 9,662,385 | B2 * | 5/2017 | Dominowski | A61K 39/0011 |

FOREIGN PATENT DOCUMENTS

| | | | |
|---|---|---|---|
| JP | 2012025684 | * | 7/2010 |
| WO | WO 2002013777 | * | 2/2002 |

OTHER PUBLICATIONS

Kessler et al (Abstr.Gen.Meet.Am.Soc.Microbiol. (93 Meet., 442, 1993).*
Zouari et al (Biomedicine & Pharmacotherapy (2016), 84, 878-891).*
Gupta et al (Indian Journal of Microbiology (2017), 57(4), 485-491).*
Langford et al. (Ann.Pharmacother. (31, No. 5, 559-63, 1997)).*

* cited by examiner

*Primary Examiner* — Jennifer E Graser
(74) *Attorney, Agent, or Firm* — Pham IP Group; Frank Huy Pham

(57) ABSTRACT

A method of treatment of pathogenic skin infectious disease using an effective antimicrobial amount of a composition of combined microorganisms comprising *Bacillus stearothermophillus* and *Bacillus subtilis* that can natural compete with pathogenic bacteria on the skin. This combination of microorganisms will utilize all limited resources that are available when there is an open wound and compete directly with pathogenic bacteria that can cause infection. Because of insufficient nutrition, the pathogenic bacteria on the skin cannot grow and therefore cannot cause infection, fungus, and other dermatology diseases that require skin nutrition to grow.

11 Claims, No Drawings

METHODS FOR TREATMENT OF SKIN INFECTIOUS DISEASES USING MICROORGANISMS

FIELD OF THE INVENTION

The invention relates to a method for treatment of skin infectious diseases using a combination of microorganisms to kill or suppress pathogenic bacteria that caused infections.

BACKGROUND OF THE INVENTION

Particular microorganisms have long been recognized as a source of skin infectious diseases. Pathogenic microorganisms cause infections by disrupting the normal functions of a host. Many pathogenic microorganisms, including intracellular bacteria, parasites, pathogenic yeast, and enveloped viruses, grow primarily in host cells where they are shielded from the effects of both antibodies and cytotoxic T cells. By developing ways to avoid the immune system, such microorganisms are able to multiply, and subsequently cause or contribute to inflammation and tissue damage in the infected organism.

As an example, tuberculosis (TB), caused by exposure to and infection with the mycobacterium, *Mycobacterium tuberculosis*, continues to infect and kill approximately 2 million people each year worldwide. It is estimated that one out of three humans are infected, leading to 8,000,000 new cases of active tuberculosis each year (Gye et al., Jama, 2822677-86, 1999). Greater knowledge of the mechanisms of human resistance to this pathogen as well as new therapeutics are needed. One of the first cell types to encounter *M. tuberculosis* after inhalation of the organism is the macrophage.

However, *M. tuberculosis* multiplies rapidly in cultured human macrophages even when they are stimulated with cytokines (Douvas et al., Infect Immun., 5021-8, 1985). Therefore, other elements of the immune system may assist macrophages in limiting the multiplication of tuberclebacilli in approximately one third of the earth's human population which is infected with *M. tuberculosis*, but does not develop active disease (Dye et al., Jama, 2822677-86, 1999).

Antimicrobial peptides are a recently discovered component of the innate immune system. They have been described in plants, tunicates, insects, fish, amphibia, and mammals, including humans, and are proposed to participate in the early host defense response against microorganisms.

They are likely to be particularly important in the early phases of defense against invading microbes because they are available within minutes to hours after the first contact with the pathogen. Moreover, the peptides exhibit a broad spectrum of activity that includes bacteria, fungi and certain enveloped viruses. Antimicrobial peptides, which numbered greater than 100 as recently as 1998, can be classified based on structural features (Hancock et al., 1995, Adv. Microb. Physiol. 372135-175; Boman 1995, Annu. Rev. Immunol. 13:61-92; and Lehrer and Ganz, 1996, Ann. Acad. Sci. 797:228-239).

However, many of these different structural classes of peptides share certain common properties. These include cationic charge, a broad spectrum of antimicrobial activity via selective discretion of target membranes, and encoding by genes which are expressed with tissue specificity.

One important element of the human innate immune defenses against microorganisms are small antimicrobial peptides known as defensins (Ganz and Lehrer, Curr Opin Immunol 10241-4, 1998). These small (30-50 aa) cationic peptides are found in a variety of mammalian myeloid and epithelial cells, and are bactericidal or bacteriostatic for a broad spectrum of microbes, including *Mycobacterium tuberculosis* (Ogata et al., Infect. Immun. 60:4720-4725, 1992; Miyakawa et al., Infect. Immun. 642926-932, 1996).

While defensins are found in rabbit (Patterson-Delafield et al., Infect Immun 312723-31, 1981) and bovine macrophages (Ryan et al., Infect. Immun. 662878-881, 1998), they are absent from human macrophages (present inventors' unpublished data). Although defensins have been proposed for use as therapeutics, chemical synthesis of these peptides is a challenge due to the complex pattern of disulfide bonds which stabilize the structure (Lauth et al., Insect Biochem Mol Biol 2821059-66, 1998), and recombinant methods do not produce sufficient yields (Harwig et al., Meth. in Enzymol. 236: 160-170, 1994; Valore and Ganz, Methods Mol Biol 782115-31, 1997).

Alternatively, using defensin proteins as antimicrobial agents was described using DNA to encode the defensins for intracellular expression in a murine macrophage cell line, which resulted in greater resistance to *Histoplasma capsulatum* (Couto et al., Injection & Immunity 62:2375-8, 1994). To date, however, there are very few reports of primary human macrophage transfection with DNA plasmids. Moreover, those which quantitate transfection efficiency report that only about 2% of the cells express the reporter gene (eGFP) (Simoes et al., J. Leulcoc Biol 651270-9, 1999; Van Tendeloo et al., Gene Ther 5:700-7, 1998; Weir and Meltzer, Cell Immunol 1482157-65, 1993).

On the other hand, the use of either bacteriostatic or bactericidal antibiotics is known to counteract bacterial infections to which humans are subjected, which may be different in nature. Although antibiotics are advantageous, they are not free from drawbacks because they generally involve side effects including imbalance of the bacterial flora of the skin, occurrence of allergic reactions, toxic effects in various districts of the organism, as well as intolerance in case of interaction with other substances, especially other drugs.

Furthermore, the overuse of antibiotics may result in the occurrence of an antibiotic resistance which can be acquired by the pathogenic agent, thus rendering ineffective the antibiotic therapy which nevertheless should be continued for a medium to long period to be successful.

In any case, the abuse of antibiotics may pose serious consequences to human organism which may even lead to death. To overcome the above drawbacks, alternative approaches to antibiotics have been investigated, particularly for the treatment of skin and mucous membranes suffering from diseases such as acne, which approaches showed the antimicrobial activity of a peptide.

Therefore, there is a need in the art for a feasible method of producing and using therapeutic antimicrobial compositions that do not naturally encounter the above problems.

SUMMARY OF THE INVENTION

The present invention pertains to method of using antimicrobial composition that combines microorganisms of *Bacillus stearothermophillus* (*B. stearothermophillus*) and *Bacillus subtilis* (*B. subtilis*) for the treatment of skin infections. The invention also pertains to a method for topical administration of the combined microorganism for treating skin infectious diseases.

On human skin and mucosal surfaces, the outcome of microbial competition determines our normal flora, which are essential for health and immune homeostasis. Colonization of normal flora by potential pathogens is the initial step in the pathogenesis of most infectious diseases (Grice et al., 2009; Hoffman et al., 2006). Efficiency of nutrient acquisition and strategies for surface attachment are essential factors for microbial niche survival, while elaboration of compounds that kill or limit the growth of competing strains or species can promote niche monopolization.

Microbes regulate and optimize their production of such molecules to kill, limit the growth of or modulate the metabolism of potential niche competitors for maximal advantage. Different factors contribute to the outcome of microbial competition, such as the collection of molecules exchanged between the competing organisms, their respective cell densities and the initial spatial configuration or direction of the microbe-microbe interaction.

Preferably, the present composition is intended for topical use on both damaged and non-damaged skin, mucous membranes including oral mucosa, and skin appendages.

Preferably, the present composition includes a mixture of microorganisms of *B. stearothermophillus* and *B. subtilis*. This combination of microorganisms directly competes with pathogenic bacteria that cause skin infections in a perpetual competition environment for suitable ecological niches to support their survival and growth.

Preferably, the present composition showed a synergistic activity, and particularly, it showed a high microbicidal action and a high ability to kill or limit the growth of competing bacterial colonization by both Gram-positive and Gram-negative, aerobic and an aerobic bacteria including, by way of a non-limiting example: *Staphylococcus Aureus, Propionibacterium acne, Pseudomonas aeruginosa, Streptococcus pyogenes, Staphylococcus epidermis*, while being simultaneously able to inhibit the degradation of skin triglyceride molecules induced by enzymes released by Gram-positive and Gram-negative, aerobic and an aerobic bacteria, thereby controlling the genesis of inflammatory process determined by the free fatty acids resulting from triglyceride hydrolysis.

Preferably, the present composition is apt to counteract bacterial infections of skin, mucous membranes and skin appendages, and it is apt to the treatment of pathologies in which a skin infection causes, or contributes to cause, detectable lesions on the skin, such as for example in acne, suppurative or non-suppurative hidradenitis, atopic dermatitis characterized by colonization by *Staphylococcus Aureus*, impetigo, interdigital infections, folliculitis, boils, post-traumatic infections, and burned skin infections.

Preferably, an objective of the present composition is to develop adaptive strategies to subsist in diverse environments to control the growth of neighboring organisms.

Preferably, another objective of the present composition is to increase the ability of the combined microorganisms to rapidly utilize all limiting resources that create antagonistic interactions with pathogenic bacteria in which the pathogenic bacteria cannot grow and therefore cannot cause infections.

Preferably, the composition is transdermally administered to the human skin in a form of lotion, in a fixed-dose of combination, *B. stearothermophillus* and *B. subtilis* formulated as a topical composition to a patient in need for the treatment of skin infections. The administration pattern of the composition comprises administering a therapeutically effective amount of the composition for at least 3 days, preferably for at least 2 days, more preferred for at least 5 days.

Preferably, the composition is administered on a daily basis and preferably twice every day. In another embodiment the composition is administered every two days and preferably once a day. In both cases, the composition is preferably administered after wash.

Preferably, the composition is applied to the human skin which contains both non-inflammation and inflammation, and in preferred embodiment of the composition is a cream or liquid spray formulation.

The term "germination enhancer" means a medium vehicle that is compatible with the skin, mucous membranes and the integuments.

The term "combination" or "mixture" should be understood as meaning a combination whose active principles are combined at fixed doses in the same vehicle/medium (single formula) that delivers them together to the point of application. Preferably, the pharmaceutical composition in the form of a fixed combination is lotion. In this case, the two active principles are dispersed and intimately mixed, during the manufacture, in the same vehicle, which delivers them together during the application of the composition.

An embodiment of the present invention further provides vehicles and vehicle components that are especially useful in the transdermal formulations, as well as concentration ranges and processing steps to obtain useful formulation forms including solids, creams, lotions, gels, and liquids.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above described exemplary embodiments, but should be defined only in accordance with the following claims appended hereto and their equivalents.

For purposes of summarizing the invention, certain aspects, advantages, and novel features of the invention have been described herein. It is to be understood that not necessarily all such advantages may be achieved in accordance with anyone particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

DETAILED DESCRIPTIONS OF THE DISCLOSURE

The present invention features a method for the treatment of skin infectious diseases by administration of a composition of microorganisms comprising *B. stearothermophillus* and *B. subtilis*. The following details a study that clearly demonstrates the clinical benefit of treatment of skin infectious diseases with microorganisms comprising *B. stearothermophillus* and *B. subtilis*.

Methods and compositions for topical administration of *B. stearothermophilus* and *B. subtilis* can successfully treat patients with skin infections. Additionally, the composition can be incorporated into solution, lotion, cream, ointment and gel formulations for application to the skin of patients with severe skin infections.

The present invention employs *Staphylococcus aureus* (*S. aureus*), a pre-eminent human pathogen causing an array of serious hospital- or community-acquired infections worldwide. At minimum, 30% of the world population is colonized with *S. aureus*, a bona fide pathogen that has developed significant resistance against a variety of antibiotics and is the cause of more fatalities in the USA than HIV/AIDS (Enright et al., 2002; Klevens et al., 2007). *S. aureus* has long been recognized as one of the most important bacteria that cause disease in humans. It is the leading cause of skin and soft tissue infections such as abscesses (boils), furuncles, and cellulitis. Although most infections are not serious, *S. aureus* can cause serious infections such as bloodstream infections, pneumonia, or bone and joint infections.

Although *S. aureus* colonizes a large proportion of the world's inhabitants, it only produces clinical infection in a subset of this population. One hypothesis is that neighboring organisms occupying the same environmental niche (e.g. skin) respond by secreting an array of antibiotic-type molecules to control *S. aureus* developmental phenotypes and thereby alter its ability to proliferate in the host. Our study reveals that *B. stearothermophillus*, occupying many environmental niches and therefore a common but transient skin microbe, can inhibit the growth of an epidemic *S. aureus* isolate and possess the ability to directionally release a molecule with antimicrobial and metabolism-altering properties.

Example 1

A clinical study of human subjects with cellulitis caused by *S. aureus* was carried out to show the effectiveness of the composition of the present invention. A fixed dose combination of microorganisms containing *B. stearothermophilus* and *B. subtilis* are topically administered at least once daily for 3 days to patients with cellulitis. At the end of the 3-day treatment period, most patients demonstrate a significant decrease in the activity of their skin infections. Formulations A, B, C and D (Table 1) were applied to each subject twice daily. Clinical appraisal was carried out at biweekly intervals.

TABLE 1

| Ingredient | % | | | |
|---|---|---|---|---|
| | A | B | C | D |
| *Bacillus stearothermolphilus* | 100 | 80 | 70 | 60 |
| *Bacillus subtilis* | — | 20 | 30 | 40 |

The results of the study are shown in Table 2 below:

TABLE 2

Clinical Evaluation of Cellulitis Treatment

| Formulation | Evaluation Time (Days) | | |
|---|---|---|---|
| | 1 | 2 | 3 |
| A | 2 | 3 | 3 |
| B | 3 | 3 | 4 |
| C | 0 | 1 | 2 |
| D | 0 | 2 | 2 |

0 = no response
1 = slight improvement
2 = good improvement
3 = very good improvement
4 = dramatic improvement The results of the foregoing tests show that increasing amount of *B. subtilis* used in the systemic treatment (formulation C and D) is ineffective. However, the results of the foregoing tests shown a good improvement with combination of less amount of *B. subtilis* and high amount of *B. stearothermophilus* (formulation B).

Example 2 (Biological "Efficacy and Safety" of the Composition of Microorganisms Containing *B. sterothermophilus* and *B. subtilis*)

The study of Example 2 is repeated to show the efficacy and safety of the composition of the present invention in the treatment of cellulitis (Table 3). Safety and tolerability were assessed through evaluations of local tolerability and adverse events. At each visit, the investigator rated erythema, scaling, dryness, swelling, and burning on a scale.

The efficacy variables were percent red area of skin reduction from baseline (total, inflammation, and non-inflammation) and subject's assessment on a scale from 0 (marked improvement) to 5 (worse).

The study conducted efficacy evaluations consisting of non-inflammation and inflammation. Table 3 is a flow chart of assessed measurements during this study.

TABLE 3

| 1 | Marked Improvement |
| 2 | Moderated Improvement |
| 3 | Minimal Improvement |
| 4 | No Change |
| 5 | Worse |

Local tolerability measures of the signs and symptoms of skin irritation were considered adverse effects only if the severity of the expected signs and symptoms was such that an interruption of the subject's participation in the study, at his/her request or at the investigator's discretion, had occurred. Altered dosing regimens (such as every other day dosing) to manage irritation were not considered to be an interruption of the subject's participation in the study.

The results of the study are shown in Table 4 below.

TABLE 4

Efficacy and Safety Measurements

Efficacy

| Formulation | Evaluation Time (Days) | | |
|---|---|---|---|
| | 1 | 2 | 3 |
| A | 2 | 2 | 2 |
| B | 2 | 2 | 1 |

TABLE 4-continued

Efficacy and Safety Measurements

| | | | |
|---|---|---|---|
| C | 4 | 3 | 2 |
| D | 4 | 4 | 3 |

Safety

Evaluation Time (Days)

| Formulation | 1 | 2 | 3 |
|---|---|---|---|
| A | 4 | 3 | 3 |
| B | 2 | 1 | 1 |
| C | 3 | 2 | 1 |
| D | 3 | 3 | 2 |

As this was an open-label study, only descriptive data presentations were made. No formal statistical hypotheses were tested. Descriptive statistics were used to summarize all data.

Treatment with the present composition for up to 3 days showed continuing improvement in reducing inflammation and/or redness starting day 3. The greatest reduction of inflammation and/or redness were seen after 3 days of treatment.

Overall improvement was observed in the subject's assessment of inflammation and/or redness. The median assessment was "Moderated Improvement" at day 2, and "Marked Improvement" at day 3.

In conclusion, the present composition was well-tolerated and effective in treatment of patients with skin infections. Signs and symptoms of skin irritation (erythema, dryness, scaling, and stinging/burning) were mostly minimum or mild and were transient.

Safety findings were consistent with the known profile of chromium. No unexpected, either systemic or dermatological, evidence of cumulative toxicity was observed over time. Consequently, extending treatment beyond 3 days does not suggest substantial additional risk for the subjects treated with present composition.

The efficacy of the present composition was also demonstrated for non-inflammatory, inflammatory and total lesions. Formulation B showed continuing reductions greater than 95% for patients with skin infections treated for 3 days.

Invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above described exemplary embodiments, but should be defined only in accordance with the following claims appended hereto and their equivalents.

Having illustrated and described the principles of the present invention in a preferred embodiment, it will be apparent to those skilled in the art that the embodiment can be modified in arrangement and detail without departing from such principles. Any and all such embodiments are intended to be included within the scope of the following claims.

What is claimed is:

1. A method for treating a disease caused by pathogenic microorganisms on a skin of a human subject that is infected by said pathogenic microorganisms, comprising topically administering an antimicrobial amount of a composition comprising from about 60% to about 80% by weight of *Bacillus stearothermophillus* and from about 20% to about 40% by weight of *Bacillus subtilis*.

2. The method of claim 1, wherein said pathogenic microorganisms comprise bacteria, fungi, parasites, and viruses.

3. The method of claim 1, wherein said disease is skin infectious disease.

4. The method of claim 3, wherein said skin infectious disease is selected from the group consisting of dermatophytosis, yeast and mycelial phase infection, opportunistic skin infections, post surgical infections, wound infections, dermatitis, impetigo, acne, dermatological condition that involve lesion on the skin, open-wound infections, or any combination thereof.

5. The method of claim 1, wherein said composition is in a form selected from the group of cream, lotion, aerosol spray, oil, or any combination thereof.

6. The method of claim 1, wherein topical administration of said composition can be selected from the group consisting of transdermal administration, topical administration, or any combination thereof.

7. A method for killing a pathogenic microorganisms on skin of a human subject comprising topically administering an antimicrobial amount of a composition comprising from about 60% to about 80% by weight of *Bacillus stearothermophillus* and from about 20% to about 40% by weight of *Bacillus subtilis*, wherein said skin of said human subject is infected by said pathogenic microorganisms.

8. The method of claim 7, wherein said pathogenic microorganisms comprises a virus.

9. The method of claim 7, wherein said pathogenic microorganisms comprises a bacteria spore.

10. The method of claim 7, wherein said pathogenic microorganisms comprises a fungus.

11. The method of claim 7, wherein said pathogenic microorganisms comprises a virus.

* * * * *